United States Patent
Thramann et al.

(10) Patent No.: US 7,101,400 B2
(45) Date of Patent: Sep. 5, 2006

(54) SHAPED MEMORY ARTIFICIAL DISC AND METHODS OF ENGRAFTING THE SAME

(75) Inventors: Jeffrey Thramann, Longmont, CO (US); Michael Fulton, Superior, CO (US)

(73) Assignee: Jeffery Thramann, Longmont, CO (US)

( * ) Notice: Subject to any disclaimer, the term of this patent is extended or adjusted under 35 U.S.C. 154(b) by 0 days.

(21) Appl. No.: 10/641,530

(22) Filed: Aug. 14, 2003

(65) Prior Publication Data

US 2004/0078080 A1 Apr. 22, 2004

Related U.S. Application Data

(60) Provisional application No. 60/404,481, filed on Aug. 19, 2002.

(51) Int. Cl.
*A61F 2/44* (2006.01)
*A61B 17/58* (2006.01)

(52) U.S. Cl. ..................... 623/17.16; 606/61
(58) Field of Classification Search .. 623/17.11–17.16; 606/61, 69, 70
See application file for complete search history.

(56) References Cited

U.S. PATENT DOCUMENTS

| | | | |
|---|---|---|---|
| 2,677,369 A | 5/1954 | Knowles | |
| 3,426,364 A | 2/1969 | Lumb | |
| 3,987,499 A | 10/1976 | Scharbach et al. | |
| 4,309,777 A | 1/1982 | Patil | |
| 4,759,769 A | 7/1988 | Hedman et al. | |
| 5,123,926 A | 6/1992 | Pisharodi | |
| 5,320,644 A | 6/1994 | Baumgarter | |
| 5,370,697 A | 12/1994 | Baumgartner | |
| 5,458,642 A * | 10/1995 | Beer et al. | 623/17.13 |
| 5,674,294 A | 10/1997 | Bainville et al. | |
| 5,676,702 A | 10/1997 | Ratron | |
| 5,827,328 A * | 10/1998 | Buttermann | 623/17.13 |
| 5,893,889 A | 4/1999 | Harrington | |
| 5,928,284 A | 7/1999 | Mehdizadeh | |
| 6,231,609 B1 | 5/2001 | Mehdizadeh | |
| 6,296,664 B1 | 10/2001 | Middleton | |
| 6,315,797 B1 | 11/2001 | Middleton | |
| 6,342,076 B1 | 1/2002 | Lundborg | |
| 6,402,785 B1 | 6/2002 | Zdeblick et al. | |
| 6,454,806 B1 | 9/2002 | Cohen et al. | |
| 6,488,710 B1 | 12/2002 | Besselink | |
| 6,491,724 B1 | 12/2002 | Ferree | |
| 6,558,423 B1 | 5/2003 | Michelson | |
| 6,620,196 B1 | 9/2003 | Trieu | |
| 6,758,683 B1 * | 7/2004 | Koopman et al. | 439/71 |
| 6,770,094 B1 * | 8/2004 | Fehling et al. | 623/17.13 |
| 2002/0116065 A1 * | 8/2002 | Jackson | 623/17.16 |
| 2003/0036798 A1 * | 2/2003 | Alfaro et al. | 623/17.16 |
| 2003/0083749 A1 * | 5/2003 | Kuslich et al. | 623/17.16 |
| 2004/0010318 A1 * | 1/2004 | Ferree | 623/17.16 |

* cited by examiner

*Primary Examiner*—David J. Isabella
(74) *Attorney, Agent, or Firm*—Holland & Hart LLP

(57) ABSTRACT

The present invention comprises an artificial disc for a spine and methods of implanting the same. The artificial disc includes an upper and lower endplate to be coupled to upper and lower vertebral bodies. A core of shaped memory alloy material is placed between the endplates to mimic the spinal disc.

14 Claims, 3 Drawing Sheets

SHAPED MEMORY ARTIFICIAL DISC AND METHODS OF ENGRAFTING THE SAME

RELATED APPLICATIONS

This application claims the benefit of U.S. Provisional Patent Application 60/404,481, filed Aug. 19, 2002, titled SHAPE MEMORY ARTIFICIAL DISC.

FIELD OF THE INVENTION

The present invention relates to artificial intervertebral discs and, more particularly, artificial intervertebral discs constructed from shaped memory alloys.

BACKGROUND OF THE INVENTION

The vertebrae of the human spine are arranged in a column with one vertebra on top of the next. Between adjacent vertebrae exists an intervertebral disc that transmits force between adjacent vertebrae and provides a cushion between the adjacent vertebrae.

Degeneration or other deformities in the intervertebral disc (the "diseased disc") can cause back pain. When a diseased disc repeatedly impinges upon neurological structures or is determined to be a pain generator, surgeons conventionally treat the diseased disc by surgically removing the diseased disc and inserting a bone graft or other device in the space vacated by the diseased disc. The adjacent vertebrae are then immobilized relative to one another with stabilization hardware. Eventually, the vertebrae grow into one solid piece of bone.

While fusing the vertebrae into one solid piece of bone is the conventional practice, fusing adjacent vertebrae into a single bone mass is a less than ideal solution. In particular, fusing two or more vertebrae into a single bone mass causes additional stress on the remaining vertebrae and discs accelerating any potential degeneration. Moreover, the fused bone mass may lead to decreased motion and flexibility in the spine. The decreased motion and/or flexibility is exacerbated when three or more vertebrae are fused.

In order to avoid fusing two or more vertebrae into a single bone mass, prosthetic devices have been developed that attempt to mimic the intervertebral disc, both size and function. The prosthetic device is implanted into the intervertebral space to replace the diseased disc. U.S. Pat. No. 5,458,642, titled SYNTHETIC INTERVERTEBRAL DISC, issued Oct. 17, 1995, to Beer et al. discloses one such prosthetic device. The Beer et al. device includes a plurality of coiled springs interspersed between two endplates. The springs of the Beer et al. device attempt to approximate the function of the replaced intervertebral disc. The Beer et al. device is less than satisfactory because the coiled springs can be damaged and lose their elasticity over time. Further, the coiled springs provide limited shock absorption requiring the use of a compressible pouch of biocompatible material to provide additional shock absorption. Moreover, adjacent vertebrae need significant separation to allow for insertion of the prosthetic device potentially causing trauma to the surrounding structures.

U.S. Pat. No. 5,676,702, titled ELASTIC DISCPROSTHESIS, issued Oct. 14, 1997, to Ratron, provides another device that attempts to mimic the replaced intervertebral disc. The Ratron device includes the same endplates separated by an elastic post and elastically deformable partitions. The Ratron device is relatively impractical, however, because the placement of the elastic post and the elastically deformable partitions is difficult and varies on a case-by-case basis. Thus, manufacturing the device prior to surgical implantation is difficult. Further, bone or other tissue growth into the intervertebral space can foul the device making it inoperable. Moreover, adjacent vertebrae need significant separation to allow for insertion of the prosthetic device potentially causing trauma to the surrounding structures. Finally, similar to springs, the elastic material may experience plastic deformation causing failure of the prosthesis. Additionally, the elastic material contained in the Ratron device may degrade over time.

While many artificial intervertebral discs exist, all of them use either coiled springs or plastics to approximate the function of the removed disc. As shown above, these artificial discs suffer many drawbacks. Thus, it would be desirous to develop an improved artificial intervertebral disc.

SUMMARY OF THE INVENTION

To attain the advantages and in accordance with the purpose of the invention, as embodied and broadly described herein, an artificial intervertebral disc is provided. The artificial intervertebral disc comprises an upper and a lower endplate. The upper and lower endplate attach to lower surface of the upper vertebral body and the upper surface of the lower vertebral body respectively. A core resides between the upper and lower endplate comprising a shaped memory alloy.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
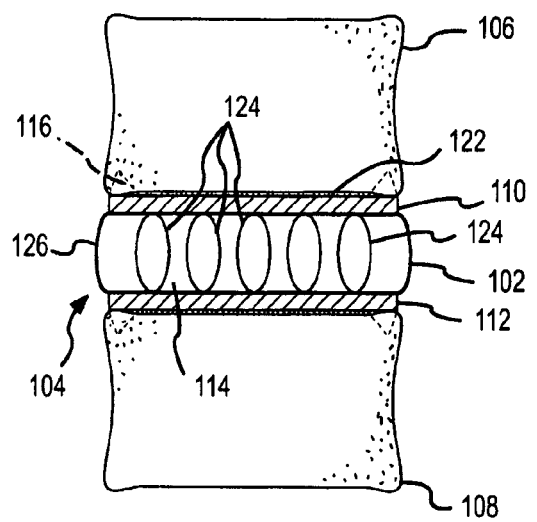
FIG. 1 is a cross-sectional, anterior view of adjacent vertebral bodies with an artificial disc consistent with an embodiment of the present invention.
Figure 2:
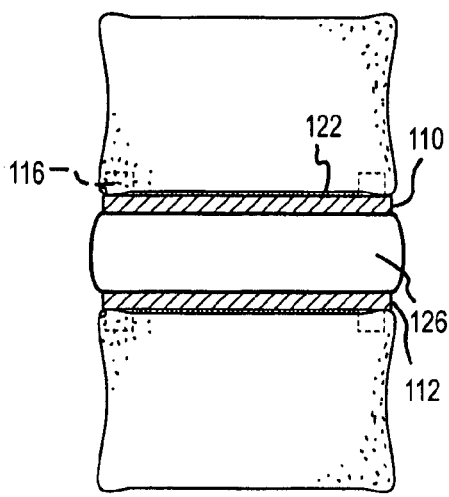
FIG. 2 is a lateral elevation view of the device of FIG. 1.
Figure 3:
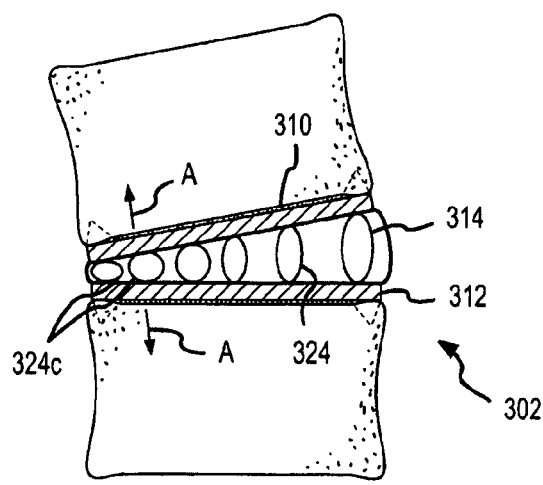
FIG. 3 is a cross-sectional, anterior view of adjacent vertebral bodies with an artificial disc consistent with another embodiment of the present invention.
Figure 4:
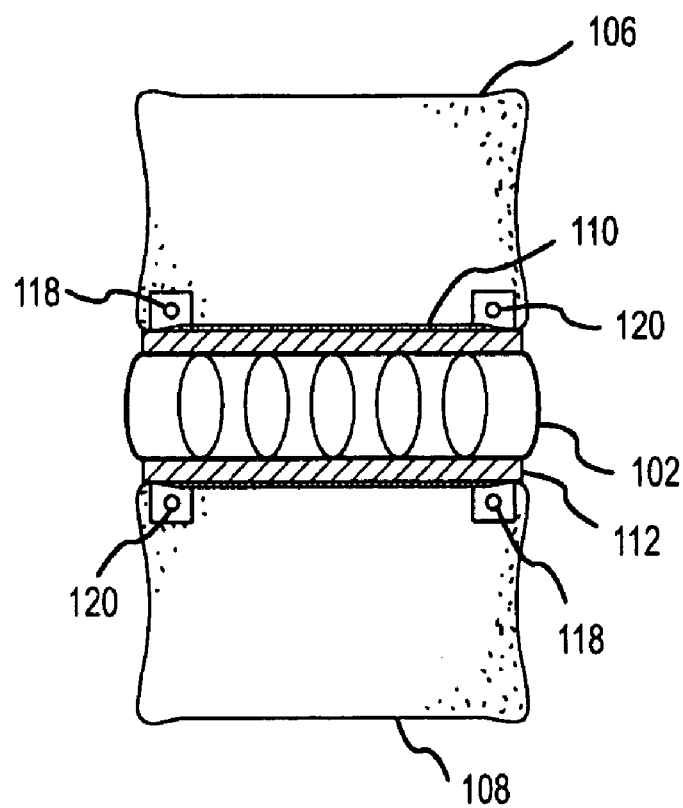
FIG. 4 is a cross-sectional, anterior view of adjacent vertebral bodies with an artificial disc consistent with another embodiment of the present invention.

Some embodiments of the present invention are described with reference to FIGS. 1 to 5. FIGS. 1–5 generally show the present invention on an eye level, off the shelf view with fixation spikes in phantom. One of skill in the art, on reading the below disclosure, will recognize that the exact configuration of the present invention will depend, in part, on the anatomy of the patient. In particular, FIG. 1 shows a cross section of an anterior view of a portion of a spinal column 100 with an artificial disc 102. FIG. 2 shows a lateral, elevation view of spinal column 100 with artificial disc 102. Disc 102 is implanted in an intervertebral space 104 situated between an upper vertebral body 106 and a lower vertebral body 108. Disc 102 includes an upper endplate 110, a lower endplate 112, and a core 114. Upper endplate 110 and lower endplate 112 should be formed of a biocompatible metal including shaped memory alloys, other metallic alloys, or plastic. Conventionally, endplates are made from titanium, but any biocompatible materials are satisfactory. If, for example, upper endplate 110 and lower endplate 112 are made from shaped memory alloys, the plates could be placed in a compact state (deformed, rolled, coiled, or the like) and activated once placed. Upper endplate 110 is coupled to upper vertebral body 106 using, for example, fixation spikes 116 (shown in phantom on FIGS. 1, 2, and 3). Fixation spikes could be replaced with screws or other conventional coupling devices. FIG. 4 shows an alternative attachment means where, for example, endplates 110 and 112 have fixation tabs 118 through which screws 120 are inserted to couple endplates 110 and 112 to upper vertebral body 106 and lower vertebral body 108.

Upper endplate 110 and lower endplate 112 are shown with a lattice and/or biochemical coating to enhance bone ingrowth and encourage longterm fixation of the plates to the vertebral bodies. Alternative to coating the plates with bone growth material 122, the plates could have other devices to encourage bone growth, such as, ridges, ribs, scars, striations, or the like. Further, a layer of adhesive or tape could be applied to assist in fixation of the plates.

Core 114 comprises a shaped memory alloy (SMA). SMAs are a group of materials that demonstrate an ability to return to some previously defined shape or size when subjected to the appropriate thermal procedure. Generally, these materials can be plastically deformed at a predefined temperature, and upon exposure to thermal manipulation, will return to the pre-deformation shape. Some SMA material is considered to be two-way shaped memory alloys because they will return to the deformed shape upon proper thermal activation. SMAs include Ag—Cd alloys, Cu—Al—Ni alloys, Cu—Sn alloys, Cu—Zn alloys, Cu—Zn—Si alloys, Cu—Zn—Sn alloys, Cu—Zn—Al alloys, In—Ti alloys, Ni—Al alloys, Ni—Ti alloys, Fe—Pt alloys, Mn—Cu alloys, Fe—Mn—Si alloys, and the like. Currently, Ni—Ti alloys (a.k.a. Nitinol) are considered a good SMA for medical applications. Making core 114 out of SMAs provides the ability to implant a compact artificial disc during the procedure requiring less distraction of upper vertebral body 106 and lower vertebral body 108. An activation signal would be provided to cause core 114 to expand to the surgically desired shape. The reduction in distraction reduces the surgical trauma associated with the implant. Many SMAs are thermally activated, however, activation signals may be any number of signals, such as, for example, thermal, electrical, magnetic, radiation, or the like.

Figure 6:
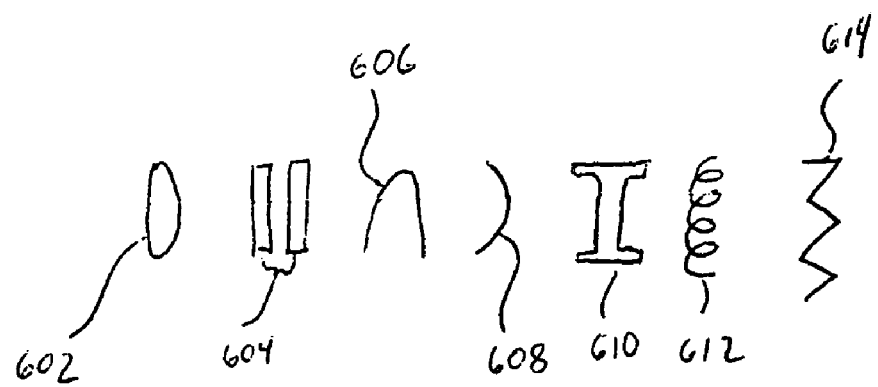
FIG. 6 is a view of possible shapes for the shaped memory alloy members 124 shown in FIG. 2.

While core 114 could be a solid piece of SMA material. It is believed core 114 would function better if core 114 comprises a series of SMA members 124 extending between upper endplate 110 and lower endplate 112. As shown, each SMA member 124 is a loop 602 (shown in FIG. 6) of SMA material to provide some vertical elastic deformation ability. As shown in FIG. 6, SMA members 124, however, could have a number of constructions, including, for example, a series of columns 604, an arc 606 or curved shape 608, a flanged surface 610 coils 612, a zigzag pattern 614, or the like. Further, each member 124 could have different or the same construction and made out of different or the same SMAs. The variation of the shapes and materials would provide surgical control of the forces associated with core 114. In particular, the SMAs could be chosen, shaped, and designed to specifically replicate and resist axial, rotational, sagital, and coronal forces using conventional design methods.

When core 114 is not a single solid piece of SMA material, a covering 126 should be deployed around core 114 to prevent tissue, scarring, or bone growth from interfering with disc 102. Covering 126 could be formed of a biocompatible metal, an alloy, or plastic. Conventionally, covering 126 would be a GORTEX® material, but any biocompatible material would function. Alternatively to covering 126, the annulus surrounding the disc could be used. In this case, the surgeon would preserve the majority of the annulus during the discectomy.

FIGS. 1 and 2 show disc 102 with a "balanced" core 114. Basically, balanced means that SMAs 124 are approximately identical. Referring specifically to FIG. 3, disc 302 is shown. Disc 302 has an "unbalanced" core 314 where the individual SMAs 324 contained in core 314 are designed with different sizes, radii, and elastic deformation coefficients. As implanted, unbalanced disc 302 applies different forces than a balanced disc would deploy. Further, because of the unique feature associated with SMA material, compact SMAs 324c could be implanted in an unexpanded state. Over time, to potentially aid in correcting spinal curvature, thermal activation of SMAs 324c could apply expansion force causing SMAs 324c to become less compact and move disc 302 from unbalanced core 314 to a more balanced core formation. The expansion of SMAs 324c would apply a force represented by Arrows A and would be designed to correct the spines curvature or the like. Alternatively to an unbalanced core, as shown in FIG. 3, multiple discs could be used aligned within the intervertebral space. Each of these multiple discs may be have a balanced core, but the core of the first disc may be different than the core of the second disc, etc., which would approximate the effect of an unbalanced core.

Figure 5:
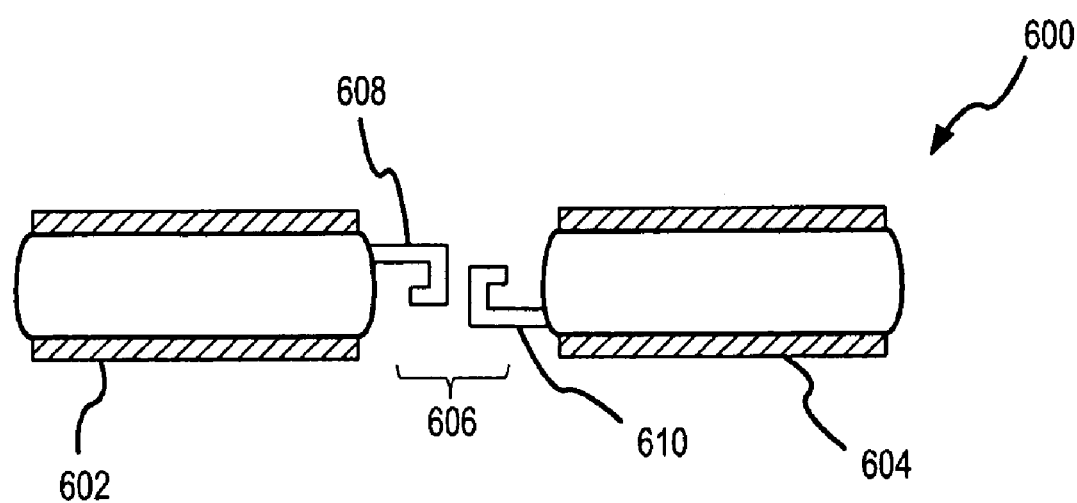
FIG. 5 is an elevations view of an artificial disc consistent with yet another embodiment of the present invention.
Figure 7:
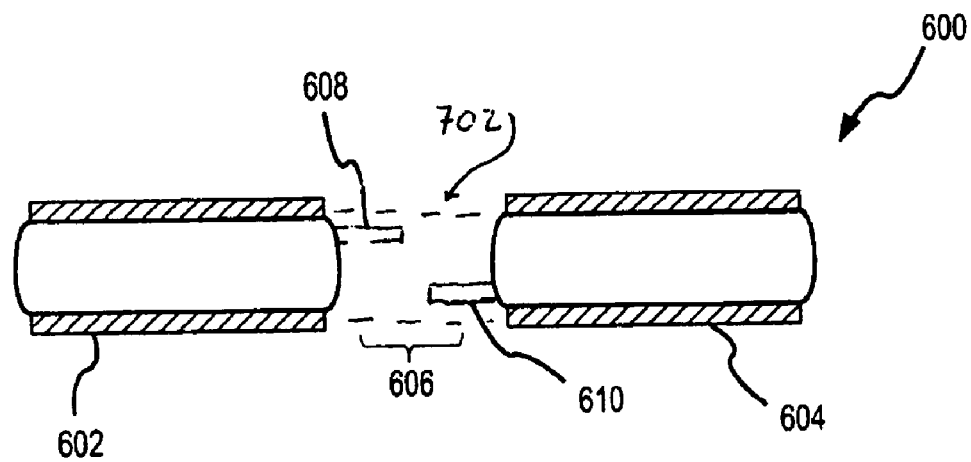
FIG. 7 is an elevations view of an artificial disc consistent of FIG. 5.

Conventionally, artificial discs are implanted using anterior surgical techniques. FIG. 5 shows that an artificial disc 600. Artificial disc 600 is essentially the same as disc 102 and disc 302. Disc 600 is divided into a first part 602 and a second part 604. Disc 600 has endplates, bone growth material, and a core similar to the above discs, and those pieces will not be re-explained here. An interlocking portion 606 has a first interlocking piece 608 attached to first part 602 and a second interlocking piece 610 attached to second part 604. While shown exploded for convenience, one of ordinary skill in the art would understand first interlocking piece 608 and second interlocking piece 610 would be intertwined to put disc 600 in a locked position 700. FIG. 7 shows disc 600 with first interlocking piece 608 and second interlocking piece 610 in an unlocked position 702 to allow relative movement between the pieces. While interlocking portion 606 is shown as a relatively simple device, one of ordinary skill in the art would recognize other more elaborate interlocking portions could be designed and used and the simple design shown is for convenience and ease of explanation. Interlocking pieces 608 and 610 can be attached to parts 602 and 604 by being a single integrated unit, screwed, glued, taped, adhered, or the like. Interlocking pieces 608 and 610 would be made of SMAs and are shown in the activated position. Activated, interlocking pieces 608 and 610 engage and hold first part 602 and second part 604 together. To install, however, interlocking pieces 608 and 610 would be in a non-activated position allowing first part 602 and second part 604 to move relative to each other. Using two halves, disc 600 can be installed from a posterior procedure. Implanting an artificial disc using a posterior procedure would be a vast improvement over current anterior implanting procedures because of the reduction in surgical trauma. Once installed, activation of interlocking portion 606 would cause the interlocking pieces 608 and 610 to engage.

While FIG. 5 shows installing two halves of an artificial disc and linking the two halves together with interlocking portion 606, it would be possible to implant several artificial disc modules in a side-by-side relation. The side-by-side modules could be linked (similar to FIG. 5) or function independently. Using several smaller modules to mimic the removed disc instead of one larger artificial disc would facilitate implantation of the artificial disc using minimally invasive techniques.

While the invention has been particularly shown and described with reference to an embodiment thereof, it will be understood by those skilled in the art that various other changes in the form and details may be made without departing from the spirit and scope of the invention.

We claim:

1. An artificial disc, comprising:
   at least one upper endplate;
   the at least one upper endplate to couple to the lower surface of an upper vertebral body;
   at least one lower endplate;
   the at least one lower endplate to couple to the upper surface of a lower vertebral body;
   at least one unbalanced core inserted into an intervertebral space between the upper endplate and the lower endplate; and
   the at least one unbalanced core comprises a plurality of independent shaped memory alloy members that extend between and contact the at leas tone upper endplate and the at least one lower endplate.

2. The artificial disc according to claim 1, further comprising:
   a plurality of fixation spikes, wherein
   at least one of the plurality of fixation spikes resides on the at least one upper endplate to couple the at least one upper endplate to the upper vertebral body and at least one of the plurality of fixation spikes resides on the at leas tone lower endplate to couple the at least one lower endplate to the lower vertebral body.

3. The artificial disc according to claim 1, further comprising:
   a plurality of fixation tabs; and
   a plurality of screws, wherein
   at least one of the plurality of fixation tabs is arranged to extend perpendicular to the at least one upper endplate and along the upper vertebral body such that a corresponding at least one of the plurality of screws can be threaded into the upper vertebral body and through the at leas tone of the plurality of fixation tables to couple the at least one upper endplate to the upper vertebral body, and wherein
   at least one of the plurality of fixation tabs is arranged perpendicular to the at least one lower endplate and along the lower vertebral body such that a corresponding at least one of the plurality of crews can be threaded into the lower vertebral body and through the at least one of the plurality of fixation tabs to couple the at least one lower endplate to the lower vertebral body.

4. The artificial disc according to claim 1, wherein each of the plurality of shaped memory alloy members comprise a loop.

5. The artificial disc according to claim 1, wherein the plurality of shaped memory alloy members comprise at least one of a series of columns, an arc, a curve, a flanged surface, a letter shape, a coil, and a zigzag pattern.

6. The artificial disc according to claim 1, wherein the at least one upper endplate comprises at least a first upper endplate and a second upper endplate the at least one lower endplate comprises at least a first lower endplate and a second lower end plate, and the at least one core comprises at least a first core and a second core, the disc further comprising:
   an interlocking portion to couple the first upper endplate, the first lower endplate, and the first core to the second upper endplate, the second lower endplate, and the second core, wherein the interlocking portion comprises a shaped memory alloy having a first unlocked position and a second locked position.

7. The artificial disc according to claim 1, further comprising:
   a covering, wherein
   the covering surrounds the core.

8. An intervertebral device to occupy a single intervertebral space, the device comprising:
   a plurality of unbalanced artificial disc modules to be inserted in a single intervertebral space, wherein:
   each of the plurality of artificial disc modules comprises:
   an upper endplate to couple to an upper vertebral body;
   a lower endplate to couple to a lower vertebral body; and
   at least one core, the at least one core comprise at least one shaped memory alloy that extends between and contacts the at least one upper endplate and the at least one lower endplate.

9. The plurality of artificial disc modules according to claim 8 wherein the at least one shaped memory alloy for each of the plurality of artificial disc modules is the same shaped memory alloy.

10. An intervertebral device to occupy a single intervertebral space, the device comprising:
    a plurality of unbalanced artificial disc modules to be inserted in a single intervertebral space, wherein:
    each of the plurality of artificial disc modules comprises:
    an upper endplate to couple to an upper vertebral body; a lower endplate to couple to a lower vertebral body; and
    at least one core, the at least one core comprise at least one shaped memory alloy that extends between and contacts the at least one upper endplate and the at least one lower endplate, wherein
    the at least one shaped memory alloy for at least one of the artificial disc modules is a different shaped memory alloy.

11. The plurality of artificial disc modules according to claim 8, further comprising:
    at least one interlocking portion between at least two of the plurality of modules.

12. An artificial disc for implantation into an intervertebral space between a first vertebral body and an adjacent second vertebral body; the artificial disc comprising:
    a plurality of unbalanced artificial disc modules to be to be inserted into a single vertebral disc space, each of the plurality of artificial disc modules comprising:
    a first endplate to couple to the first vertebral body, the first endplate prepared to enhance long term fixation of the first endplate to the first vertebral body;

a second endplate to couple to the second vertebral body, the second endplate prepared to enhance long term fixation of the second endplate to the second vertebral body; and a plurality of shaped memory alloy cores, each of the shaped memory alloy cores having a first end abutting the first endplate and a second end abutting the second endplate when implanted, wherein the shaped memory alloy cores are designed to mimic an intervertebral disc.

13. The artificial disc according to claim 12, wherein the preparation of the first endplate and the second endplate to enhance long term fixation comprises at least one of a coating of bone growth material, at least one spike, or a plurality of striations.

14. The artificial disc according to claim 12, wherein the at least one shaped memory alloy comprises a plurality of shaped memory alloy members, and the plurality of shaped memory alloy members comprises at least one of a loop, a coil, an arc, a zig-zag, a post, a column, a letter shape, a flanged shape, and a curve.

* * * * *